United States Patent
Borchardt et al.

(10) Patent No.: US 9,774,589 B2
(45) Date of Patent: Sep. 26, 2017

(54) MANAGEMENT METHOD AND ARRANGEMENT FOR OUTPATIENT ELECTROCARDIOGRAPHY ON A PATIENT

(71) Applicant: GETEMED MEDIZIN—UND INFORMATIONSTECHNIK AG, Teltow (DE)

(72) Inventors: Tilo Borchardt, Meerane (DE); Winfried Scharner, Aue (DE); Michael Scherf, Berlin (DE); Robert Downes, Kleinmachnow (DE)

(73) Assignee: GETEMED MEDIZIN—UND INFORMATIONSTECHNIK AG, Teltow (DE)

( * ) Notice: Subject to any disclaimer, the term of this patent is extended or adjusted under 35 U.S.C. 154(b) by 148 days.

(21) Appl. No.: 14/927,081

(22) Filed: Oct. 29, 2015

(65) Prior Publication Data
US 2016/0127354 A1    May 5, 2016

(30) Foreign Application Priority Data
Oct. 30, 2014   (DE) .......................... 10 2014 222 220

(51) Int. Cl.
*G06F 3/00*     (2006.01)
*H04L 29/06*    (2006.01)
(Continued)

(52) U.S. Cl.
CPC ........ *H04L 63/0823* (2013.01); *A61B 5/0006* (2013.01); *A61B 5/0432* (2013.01);
(Continued)

(58) Field of Classification Search
CPC .. H04L 63/0823; H04L 63/102; H04W 12/06; H04W 12/08
See application file for complete search history.

(56) References Cited

U.S. PATENT DOCUMENTS

2009/0171227 A1* 7/2009 Dziubinski .......... A61B 5/0452
                                                    600/516
2009/0292340 A1* 11/2009 Mass .................. A61N 1/37282
                                                    607/60
(Continued)

OTHER PUBLICATIONS

Access control over authentication, Vieweg und Teubner, 2010. S. 127-157. (English Abstract).
(Continued)

*Primary Examiner* — Joseph P Hirl
*Assistant Examiner* — Sayed Beheshti Shirazi
(74) *Attorney, Agent, or Firm* — Maschoff Brennan

(57) ABSTRACT

A management method for outpatient electrocardiography on a patient using an ECG recorder, an administration network, a first mobile device and at least one second mobile device is provided. In order to initialize outpatient electrocardiography on a patient, the first mobile device is connected to the ECG recorder and to the administration network and in the process an identification code assigned to the ECG recorder is transmitted from the ECG recorder to the administration network. After the verification of the authorizations of the mobile device, at least one certificate assigned to the ECG recorder is provided by the administration network and is transmitted to the ECG recorder for storage via the mobile device. The second mobile device is connected to the ECG recorder and to the administration network and in the process the identification code assigned to the ECG recorder is transmitted from the ECG recorder to the administration network.

17 Claims, 3 Drawing Sheets

(51) Int. Cl.
*A61B 5/0432* (2006.01)
*A61B 5/00* (2006.01)
*H04W 12/06* (2009.01)
*H04W 12/08* (2009.01)

(52) U.S. Cl.
CPC ........... *H04L 63/102* (2013.01); *H04W 12/06* (2013.01); *H04W 12/08* (2013.01)

(56) References Cited

U.S. PATENT DOCUMENTS

| | | | |
|---|---|---|---|
| 2010/0045425 A1* | 2/2010 | Chivallier | A61B 5/0002 340/5.8 |
| 2011/0145894 A1* | 6/2011 | Garcia Morchon | G06F 19/3412 726/4 |
| 2011/0197067 A1* | 8/2011 | Corndorf | H04L 9/0844 713/172 |
| 2013/0085364 A1* | 4/2013 | Lu | A61B 5/0022 600/384 |
| 2013/0212381 A1* | 8/2013 | Bousamra | H04L 63/0823 713/156 |
| 2014/0288947 A1* | 9/2014 | Simpson | G06F 19/3418 705/2 |
| 2014/0350955 A1* | 11/2014 | Yedidsion | G06F 19/3418 705/2 |
| 2015/0161339 A1* | 6/2015 | Teucher | G06F 19/3456 604/504 |

OTHER PUBLICATIONS

CardioMem CM 4000, Product Information, retrieved from http://www.getemed.net/en/cardiology/cardiomemr-cm-4000/ on Oct. 29, 2015.

* cited by examiner

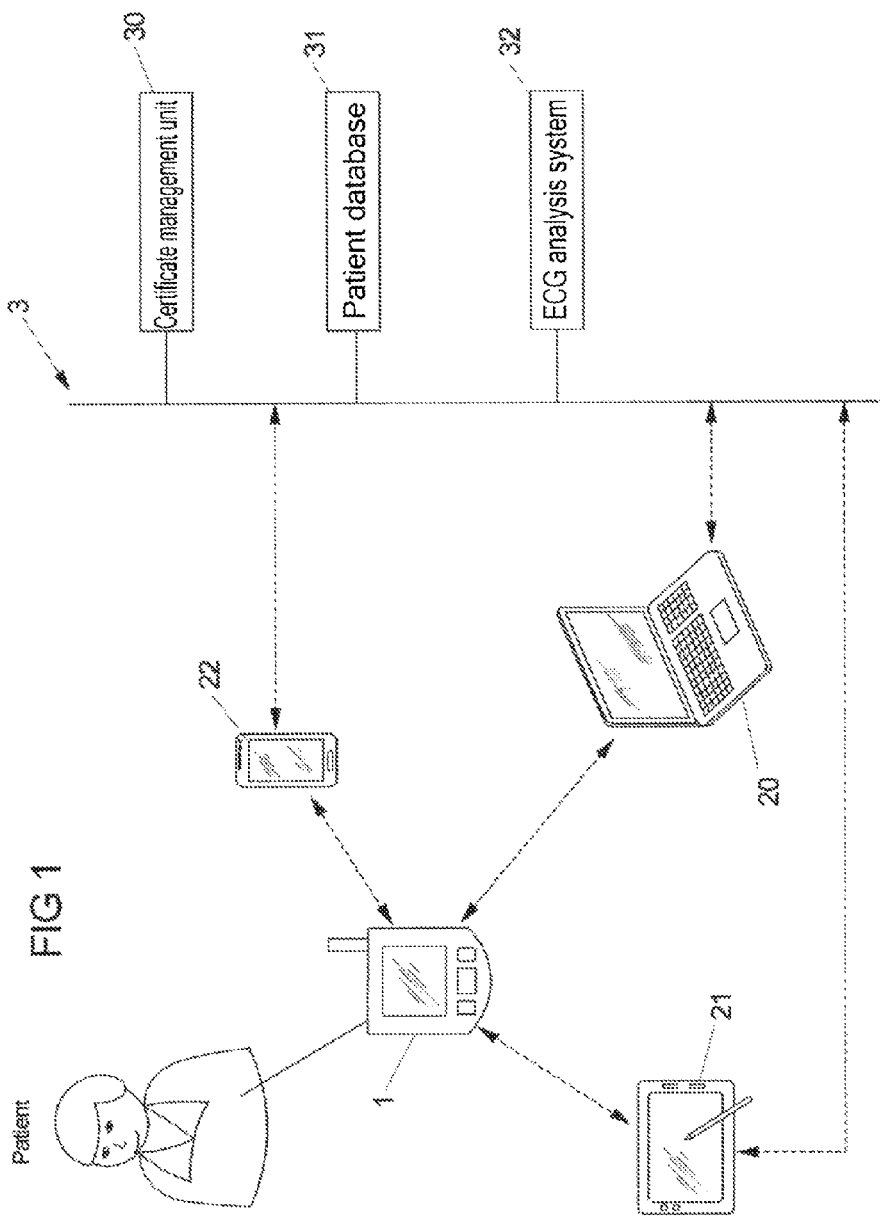

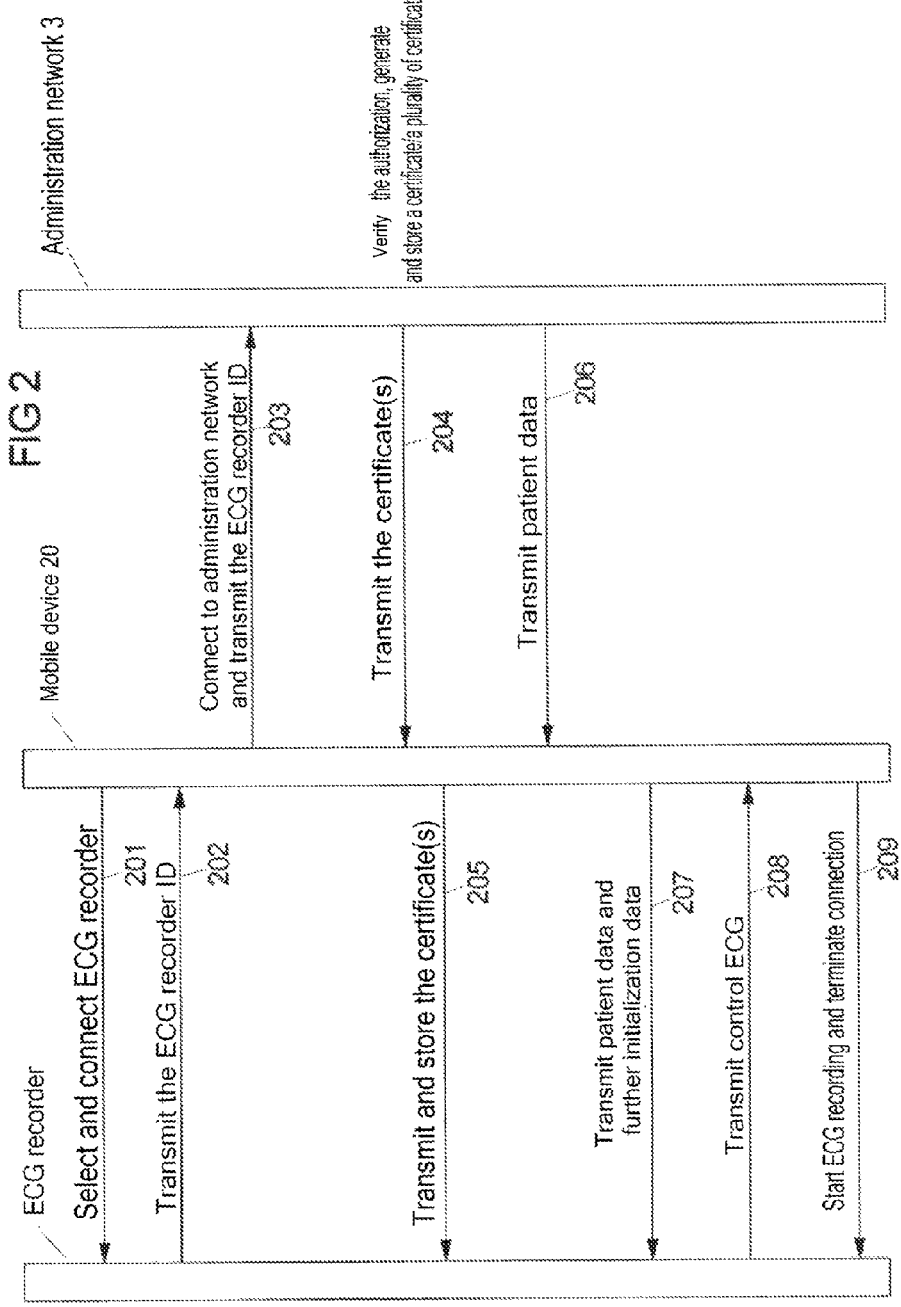

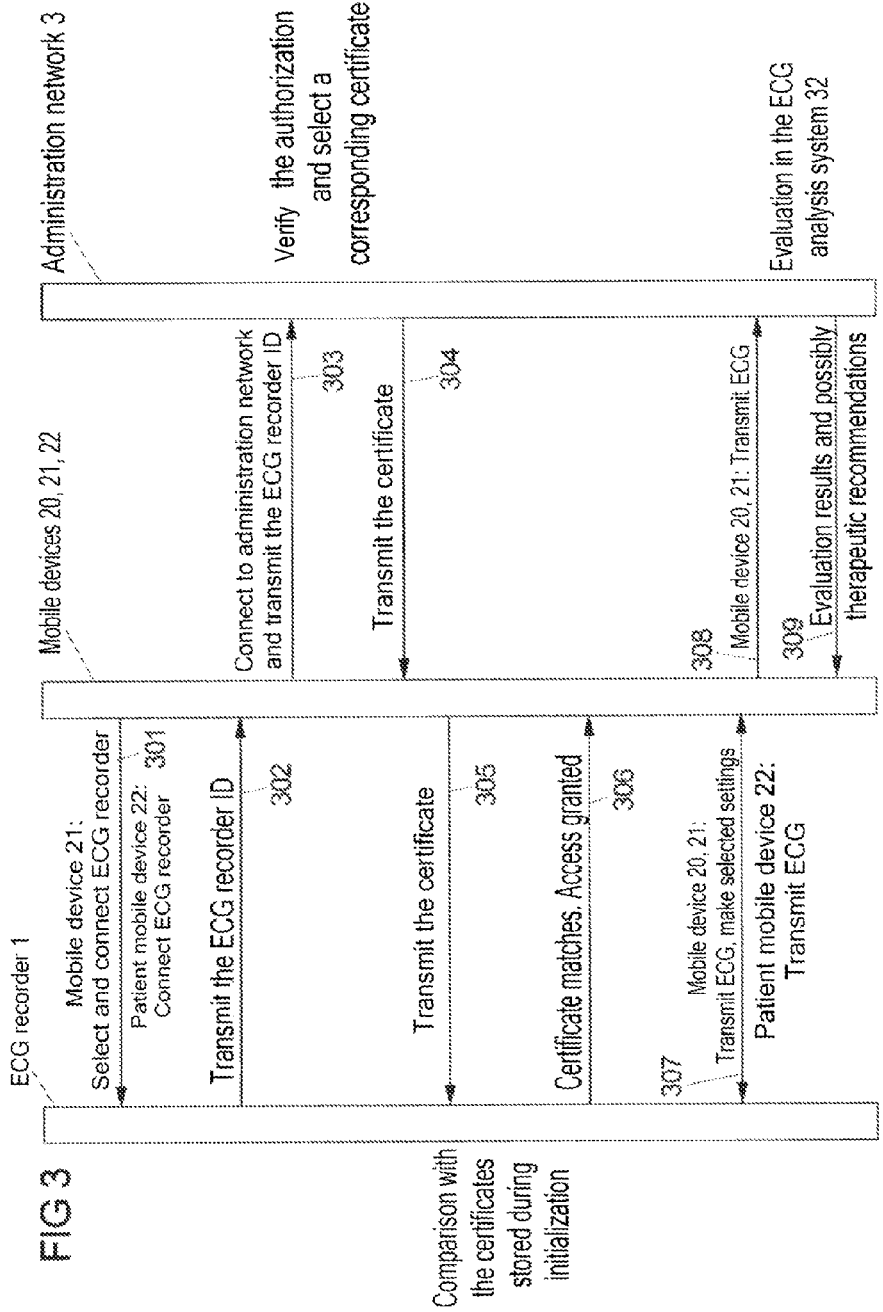

MANAGEMENT METHOD AND ARRANGEMENT FOR OUTPATIENT ELECTROCARDIOGRAPHY ON A PATIENT

RELATED APPLICATION

This patent application claims priority to German patent application no. 10 2014 222 220.6, filed Oct. 30, 2014, which is incorporated herein by reference.

BACKGROUND

The invention relates to a management method and arrangement for outpatient electrocardiography (ECG) on a patient.

It is known practice to record an electrocardiogram (ECG) over a relatively long period of, for example, 12 hours, 24 hours or else 7 days and to then read and evaluate the electrocardiogram. Such a long-term ECG is used, for example, to enable better detection and assessment of arrhythmias. In addition, electrocardiography methods are also known in which individual shorter ECG sections are recorded as a so-called event ECG according to stipulated time specifications and/or after manual or automatic triggering during the occurrence of specific events such as palpitations or skipped heartbeats and are transmitted to a doctor or a medical centre, possibly in a trans-telephonic manner, for evaluation. In the text below, the term "outpatient electrocardiography" should be understood as meaning both long-term ECGs and event ECGs for recording shorter sections and combinations of both variants.

In order to record an outpatient ECG, it is known practice to use portable ECG recorders which can be connected to electrodes fitted to the patient via discharge cables. However, for event ECGs in particular, ECG recorders are also known which, for the purpose of recording an ECG section using electrodes formed thereon, can be brought into contact with the patient directly, that is to say without discharge cables. In the text below, the term "ECG recorder" should be understood as meaning both of said variants of ECG recording devices, that is to say those with electrodes formed thereon for directly taking an ECG on the patient and those which, in order to take an ECG, can be connected to electrodes fitted to the patient via discharge cables.

For example, GETEMED Medizin- und Informationstechnik AG in 14513 Teltow produces a recorder for recording long-term ECGs under the name CardioMem CM 4000. This recorder comprises a large colour display which displays relevant information including the ECG profile. However, ECG recorders are also known which do not have any operating elements for direct input and do not have a display for displaying relevant information, but rather are connected to external devices for the purpose of operation or communication.

When initializing an outpatient ECG using such an ECG recorder, a so-called "hook-up" to a control ECG is generally carried out before the actual recording. Depending on the embodiment of the ECG recorder, the hook-up can be carried out directly on the ECG recorder using operating elements provided thereon and a display or alternatively using a PC or notebook connected to the ECG recorder or a mobile device (for example a tablet PC or smartphone) which is connected to the ECG recorder and on which special software is installed for this purpose.

In the case of a conventional variant of initializing an ECG, in which the hook-up is carried out using a mobile device connected to the ECG recorder, the information and settings which are required for the ECG recording and are matched to the patient are generally first of all transmitted from the mobile device to the ECG recorder. Furthermore, the correct function of the ECG recording is usually verified using a control ECG. Only then is the actual ECG recording started.

In this case, in particular, a mobile device can be connected to the ECG recorder wirelessly, for example via Bluetooth or WLAN, for the purpose of initialization or displaying the ECG profile.

It must be ensured in this case, for reasons of security and data protection, that users of mobile devices, on which the corresponding application software ("app") which can be obtained by anyone online is installed, only gain access to the control of the ECG recorder or to the data relating to the ECG profile which are stored thereon according to their respective provided authorizations. This is very important, in particular, during such medical use in which sensitive patient data are generated, stored and used. Without further precautions for safeguarding security and data protection, unauthorized parties could download a corresponding app from the Internet and could possibly carry out dangerous interventions in the ECG recordings or unauthorized access to patient data.

SUMMARY

The present invention is based on the object of providing a management method and arrangement for outpatient electrocardiography on a patient, which method and arrangement allow flexible access to an ECG recorder by a plurality of mobile devices while simultaneously safeguarding security and data protection.

This object is achieved by means of a management method for outpatient electrocardiography having the features as described herein and a management arrangement for outpatient electrocardiography having the features as described herein.

Accordingly, the management arrangement for outpatient electrocardiography comprises an ECG recorder and a first mobile device which can be wirelessly connected to the ECG recorder, wherein a software for initializing and controlling the ECG recorder and for displaying the ECG profile is installed on the mobile device. The arrangement also comprises an administration network which can be connected to the mobile device, verifies, before the ECG recorder is initialized by the first mobile device, its authorization for the initialization and generates at least one certificate which is assigned to the ECG recorder and is transmitted to the ECG recorder for storage via the first mobile device. In the sense of the invention, the administration network may comprise in this case a plurality of networked units or only a single unit, for example a server.

At least one second mobile device which can be wirelessly connected to the ECG recorder and has software installed thereon for controlling the ECG recorder and/or for displaying the ECG profile is also provided, which second mobile device is designed, after a verification of its authorization by the administration network, to receive the at least one certificate assigned to the ECG recorder from the administration network and to use this certificate to gain access to the ECG recorder in order to control the latter and/or to display the ECG profile.

The management method for outpatient electrocardiography provides for authorizations of the different mobile devices to be stored in an administration network. In order to initialize outpatient electrocardiography on a patient, the first mobile device is connected to the ECG recorder and to the administration network and in the process an identification code assigned to the ECG recorder is transmitted from the ECG recorder to the administration network via the mobile device. After a verification of the authorizations of the mobile device, at least one certificate assigned to the ECG recorder is provided by the administration network and is transmitted to the ECG recorder for storage via the mobile device.

In order to check the progress of the ECG and/or for diagnosis, the second mobile device is connected to the ECG recorder and to the administration network. The identification code assigned to the ECG recorder is transmitted from the ECG recorder to the administration network via the second mobile device. According to the authorizations of the second mobile device, one of the previously generated certificates assigned to the ECG recorder is then transmitted from the administration network to the second mobile device. This certificate is transmitted from the second mobile device to the ECG recorder. After comparison with the certificate previously transmitted by the first mobile device, access by the second mobile device for the purpose of controlling the ECG recorder and/or displaying the ECG profile is enabled according to the authorizations of the second mobile device.

The solution according to the invention is therefore based on the concept of enabling, in principle, access to the ECG recorder by a plurality of mobile devices in a flexible manner for the purpose of control and/or displaying the ECG profile and of simultaneously safeguarding the high requirements imposed on safety and data protection in the medical sector by virtue of the authorization for accessing the ECG recorder being provided by an administration network using certificates.

Avoiding user-specific passwords therefore advantageously achieves flexibility in the access to different ECG recorders by different authorized persons having different mobile devices, as is desirable in a clinic, for example. For example, a plurality of doctors whose different mobile devices are stored in the administration network with particular authorizations can access different ECG recorders according to their respective authorizations.

In particular, in addition to the initialization of an ECG recording, it is possible, according to the inventive solution, to gain access to the ECG recorder and to view the ECG profile even during the ongoing ECG recording. This can be used for a quality check of the ECG recording or already for diagnostic purposes.

In one advantageous refinement, the authorizations of the mobile devices, which are stipulated in the administration network, determine which mobile devices are allowed to gain access to which functions of an ECG recorder. In this manner, no security risk occurs even if a mobile device is lost. All authorizations can be withdrawn from a mobile device reported as lost at the level of the administration network. It is then no longer possible to access the ECG recorder since the certificates used for authorization are preferably not stored on the mobile device but rather have to be transmitted again, before each access attempt, from the administration network to the mobile device and from there onwards for the purpose of comparison with certificates stored in the ECG recorder.

In one exemplary embodiment, the mobile devices are identified inside the administration network using identification codes (for example serial numbers) which are assigned to the mobile devices and are transmitted from the mobile devices to the administration network when making the connection.

Another aspect of the invention provides for a mobile device to be assigned to the patient as a patient mobile device. The authorizations allocated to the patient mobile device inside the administration network are restricted here to the display of the ECG profile in a framework stipulated for the patient. This has the advantage that an interested patient or possibly even a technically accomplished patient can inspect the ECG profile. In the event of faults which would otherwise not be readily perceived by the patient (for example electrodes which have fallen off or have not been correctly fitted), service advice can be additionally given by the software on the patient mobile device.

One exemplary embodiment of the invention provides for the different mobile devices to use the same application software which can be downloaded from the Internet for the purpose of initializing and/or controlling the ECG recorder and/or displaying the ECG profile, and for their different authorizations to be implemented by the ECG recorder using the certificate which is provided for the respective mobile device by the administration network.

In particular, one advantageous refinement of the method according to the invention may provide for the administration network to provide two different certificates for each ECG recording, one certificate being a patient certificate assigned to the patient mobile device.

It is also within the scope of the invention that provision may be made for the administration network to provide a certificate for each ECG recording, which certificate is used by all mobile devices for authorization for accessing the ECG recorder, in which case possibly different authorizations of the mobile devices are implemented at the level of the application software for initializing and/or controlling the ECG recorder and/or for displaying the ECG profile by virtue of a corresponding patient app with reduced functionality being installed on the patient mobile device and a corresponding service app being installed on the other mobile devices, in particular.

Furthermore, provision may be made for the patient mobile device to be used for the GPS positioning of the patient so that medical staff can help in the case of critical complications, for example.

According to one advantageous refinement of the method according to the invention, in order to initialize the outpatient electrocardiography, the patient data required for this purpose are transmitted from a patient database inside the administration network to the first mobile device and are transmitted from there to the ECG recorder.

Furthermore, provision may be made, when initializing the outpatient electrocardiography, for the safe application of the ECG electrodes to be checked and for an error message including instructions for error correction to possibly be transmitted to the first mobile device.

Another aspect of the invention provides for the ECG data to be transmitted from the ECG recorder to an ECG analysis system inside the administration network via the mobile devices for evaluation, the evaluation results, possibly including therapeutic recommendations, in turn being transmitted from the ECG analysis system to the mobile devices.

In one advantageous refinement of the invention, a near-field communication method, in particular Bluetooth or WLAN, is used to transmit data between the mobile devices and the administration network and/or between the mobile devices and the ECG recorder.

Data are advantageously transmitted between the mobile devices and the administration network and/or between the mobile devices and the ECG recorder in encrypted form, in particular using two-fish encryption or the HTTPS protocol.

In one advantageous refinement of the method according to the invention, the ECG data and the certificates are stored in the ECG recorder and in the administration network in encrypted form.

Another exemplary embodiment of the invention provides for the certificates provided by the administration network to be generated for a respective ECG recording as temporary certificates with a stipulated validity period.

Furthermore, provision may be made for the certificates provided by the administration network for an ECG recording using an ECG recorder to be deleted after data have been transmitted to the ECG analysis system. This ensures that, if the ECG recorder is passed on to another patient, no misuse or errors with respect to the assignment of the data and settings may arise.

According to one advantageous refinement of the arrangement according to the invention, a patient mobile device which is assigned to the patient, can be wirelessly connected to the ECG recorder and has software installed thereon for displaying the ECG profile is provided, which patient mobile device is configured, after a verification of its authorizations by the administration network, to receive the or one of the certificates assigned to the ECG recorder from the administration network as a patient certificate and to gain access to the ECG recorder in a particular stipulated framework for the purpose of displaying the ECG profile.

Another aspect of the arrangement according to the invention provides for the administration network to comprise a patient database from which, during the initialization of the outpatient electrocardiography, the patient data required for this purpose are transmitted to the first mobile device and from there to the ECG recorder.

It is within the scope of the invention that the administration network comprises an ECG analysis system to which the ECG data can be transmitted from the ECG recorder via the mobile devices for evaluation, the evaluation results in turn being able to be transmitted from the ECG analysis system to the mobile devices.

BRIEF DESCRIPTION OF THE DRAWINGS

The invention is explained in more detail below with reference to the figures of the drawings.

FIG. 1 shows a schematic management arrangement for outpatient electrocardiography on a patient.

FIG. 2 shows a flowchart for initializing outpatient electrocardiography on a patient using a mobile device.

FIG. 3 shows a flowchart for checking the progress of outpatient electrocardiography on a patient using a second mobile device.

DETAILED DESCRIPTION

FIG. 1 shows a management arrangement for outpatient electrocardiography on a patient, as can be advantageously used by a clinic or doctor's surgery, for example.

In the exemplary embodiment illustrated, the arrangement comprises an ECG recorder 1 which can be connected to a patient using ECG electrodes and possibly discharge cables, a first mobile device 20 (for example the notebook belonging to a doctor), a second mobile device 21 (for example the tablet PC belonging to a further doctor) and a patient mobile device 22 (for example the smartphone belonging to the patient), special software for initializing and controlling the ECG recorder 1 and/or for displaying the ECG profile respectively being installed on the mobile devices 20, 21, 22. The mobile devices 20, 21, 22 can be connected to the ECG recorder wirelessly, for example via Bluetooth or WLAN. The arrangement also comprises an administration network 3 which can be connected to the mobile devices and may be, for example, a secured medical network protected by a firewall. The administration network 3 comprises a certificate management unit 30 in which the mobile devices 20, 21, 22 are stored, for example with their serial number, and are each assigned to particular authorizations with respect to access to the ECG recorder 1. The administration network 3 also comprises a patient database 31 which stores information relevant to the ECG recording. A workstation 32 for analysing the outpatient ECG is also provided in the administration network 3. In this case, the patient database 31 may also be part of the ECG analysis system 32.

The method according to the invention for flexibly managing an outpatient ECG while safeguarding security and data protection is illustrated below.

FIG. 2 shows a flowchart for initializing an outpatient ECG using a mobile device. For this purpose, an authorized user of the mobile device 20, for example a doctor, first of all selects the ECG recorder 1 from a list of possibly a plurality of ECG recorders in the near field (typically in Bluetooth range) using the software installed on the mobile device 20, and the mobile device 20 connects to the ECG recorder 1 (step 201). The identification code (for example the serial number) of the ECG recorder is transmitted to the mobile device 20 (step 202). The mobile device 20 then connects to the administration network 3 and transmits the identification code of the ECG recorder 1 to the administration network 3 (step 203) which comprises a certificate management unit 30. The transmitted identification codes are used inside the certificate management unit 30 of the administration network 3 to verify whether the mobile device 20 has the authorization to initialize an outpatient ECG recording using the ECG recorder 1. If so, at least one certificate is generated, is transmitted from the administration network 3 to the mobile device 20 (step 204) and is transmitted from there to the ECG recorder 1 for storage (step 205).

The patient data required for initializing the outpatient ECG are then transmitted from the patient database 31 of the administration network 3 to the ECG recorder 1 via the mobile device 20 (steps 206, 207). During the initialization, various settings such as the recording time and duration and the number of ECG channels can be made (step 207). In this case, relevant data relating to the ECG recorder 1, for example the serial number or the battery status, can be displayed using the software installed on the mobile device 20. Before the actual ECG recording is started, an automated check of the safe application of the ECG electrodes to the patient's body can be carried out and an error message including instructions for error correction can possibly be transmitted to the first mobile device 20 and can be displayed using the software installed on the latter. A control ECG is transmitted from the ECG recorder 1 to the mobile device 20 and is displayed there (step 208). The ECG recording is then started by the mobile device 20 and the connection between the mobile device 20 and the ECG recorder 1 is terminated (step 209), thus concluding the initialization of the outpatient electrocardiography.

The solution according to the invention advantageously allows a plurality of authorized persons (for example selected doctors) with different mobile devices 20, 21 in the vicinity, for example in a clinic, to gain access to the ECG recorder 1 in order to view and evaluate an ongoing ECG recording over a limited period. In this case, provision may also be made for an authorized group of people to be able to interrupt the ECG recording, for example for an MRT examination.

The patient can also be optionally included in the management of the outpatient electrocardiography within certain limits. The patient mobile device 22 is used for this purpose.

Special software may be provided for the patient mobile device 22 as a patient app, the functionality of which is restricted in comparison with a service app used by the medical staff. The patient app may be, in particular, a suitably modified service app.

In another variant, the different mobile devices 20, 21 and the patient mobile device 22 may use the same software which can be downloaded from the Internet, in which case their different authorizations are implemented by the ECG recorder 1 using the certificate provided for the respective mobile device 20, 21 or patient mobile device 22 by the administration network. In particular, provision may be made for a special patient certificate to be generated for the patient mobile device 22.

The functionality of the patient mobile device 22 with regard to accessing the ECG recorder 1 may be restricted, for example, to the display of the battery status and the presentation of the ECG. The presentation of the ECG is suitable for patients who can interpret an ECG. In addition, provision may also be made for the patient to be able to interrupt or abort the ECG recording using the patient mobile device 22 and the software installed on the latter. Provision may also be made for a connection to be able to be set up to a medical service centre or the clinic or doctor's surgery during the ECG recording using the patient mobile device. Behavioural and diagnostic information as well as therapeutic recommendations can then be transmitted from the service centre. It is also conceivable to enable verbal communication between patients and the service centre using the patient mobile device 22. A further function of the patient mobile device 22 may involve the ability to determine the whereabouts of the patient and to communicate them in an emergency using GPS or similar services.

FIG. 3 shows a flowchart for checking the progress of outpatient electrocardiography previously initialized by a first mobile device 20 using this mobile device or a second mobile device 21, 22 which may be, for example, a mobile device 21 belonging to a doctor or the patient mobile device 22.

For this purpose, the user of a mobile device 20, 21 (for example a doctor) selects the ECG recorder 1 from a list of possibly a plurality of ECG recorders in the near field using the service app installed on the mobile device and establishes a wireless connection, for example via Bluetooth (step 301). If the patient accesses the ECG recorder 1, the patient mobile device 22 is wirelessly connected to the ECG recorder 1. In the next step (302), the identification code of the ECG recorder 1 is transmitted to the mobile device 21 or to the patient mobile device 22 (mobile device 20, 21, 22 below). The mobile device 20, 21, 22 connects to the administration network 3 and transmits the identification code of the ECG recorder 1 to the administration network 3 (step 303). The authorization of the respective mobile device 20, 21, 22 is verified in the certificate management unit 30 of the administration network 3 and, if authorization is present, one of the previously generated certificates assigned to the ECG recorder 1 is transmitted from the administration network 3 to the mobile device 20, 21, 22 according to the authorizations of the mobile device 20, 21, 22 (step 304). In the next step (305), the certificate is transmitted from the mobile device 20, 21, 22 to the ECG recorder 1 where a comparison with the at least one certificate previously transmitted by the first mobile device 20 takes place. If the certificate does not match, access is denied and the connection is interrupted. If the certificates match, the mobile device 20, 21, 22 is allowed to access the ECG recorder 1 according to the authorizations of the mobile device 20, 21, 22 which are coded in the respective certificate (step 306). For example, provision may be made for the patient to be able to transmit the ECG from the ECG recorder 1 to his patient mobile device 22 and to display it using the software installed on the latter (step 307). Authorized doctors or members of the medical staff trained for this purpose can possibly additionally make certain settings on the ECG recorder 1 using the corresponding mobile devices 20, 21 (step 307) or can transmit the ECG to the ECG analysis system 32 in the administration network 3 for evaluation (step 308) and can view the results of this evaluation, possibly including therapeutic recommendations, on their mobile devices 20, 21 (step 309).

After the transmission of the ECG recording from the ECG recorder 1 to the ECG analysis system 32 has been concluded, all certificates provided by the administration network for the ECG recording using an ECG recorder 1 are automatically deleted. This ensures that, if the ECG recorder is passed on to another patient, no misuse or errors with respect to the assignment of the data and settings may arise.

In order to safeguard data security, the data connection between the mobile devices 20, 21, 22 and the administration network 3 and/or between the mobile devices 20, 21, 22 and the ECG recorder 1 is encrypted in one advantageous embodiment, for example using two-fish encryption or the HTTPS protocol. The ECG data and the certificates can also be advantageously stored in the ECG recorder 1 and in the administration network 2 in encrypted form.

The configuration of the invention is not only restricted to the exemplary embodiments which are described above and should be understood only as examples.

LIST OF REFERENCE SYMBOLS

1 ECG recorder
20 Mobile device
21 Mobile device
22 Patient mobile device
3 Administration network
30 Certificate management unit
31 Patient database
32 ECG analysis system

The invention claimed is:

1. A management method for outpatient electrocardiography on a patient which method, with the use of an electrocardiography (ECG) recorder, an administration network, a first mobile device and at least one second mobile device, wherein software for initializing an controlling the ECG recorder and/or for displaying the ECG profile is installed on the mobile devices, comprises the following steps:
   storing the mobile devices in the administration network as mobile device each with stipulated authorizations;
   connecting the first mobile device to the ECG recorder and to the administration network for initializing outpatient electrocardiography on a patient;

in the process transmission of an identification code assigned to the ECG recorder from the ECG recorder to the administration network via the first mobile device, and, after a verification of the authorizations of the first mobile device by the administration network, providing at least one certificate assigned to the ECG recorder by the administration network which is transmitted to the ECG recorder for storage via the first mobile device;

connecting a second mobile device to the ECG recorder and to the administration network, so that the profile of the ECG can be checked and/or displayed by the second mobile device;

in the process transmission of the identification code assigned to the ECG recorder from the ECG recorder to the administration network via the second mobile device; and transmission of one of the previously generated certificates assigned to the ECG recorder from the administration network to the second mobile device according to the authorizations of the second mobile device; and transmission of this certificate from the second mobile device to the ECG recorder and, after a comparison with the at least one certificate previously transmitted by the first mobile device, enabling the access by the second mobile device for the purpose of controlling the ECG recorder and/or displaying the ECC profile according to the authorizations of the second mobile device.

2. The method according to claim 1, wherein the authorizations of the mobile devices, which are stipulated in the administration network, determine which mobile devices are allowed to gain access to which functions of the ECG recorder.

3. The method according to claim 1, wherein the mobile devices are identified inside the administration network using identification codes which are assigned to the mobile devices and are transmitted from the mobile devices to the administration network when making the connection.

4. The method according to claim 1, wherein one of the second mobile devices is assigned to the patient as a patient mobile device, the authorizations allocated to the patient mobile device in the administration network being restricted to the display of the ECG profile in a framework stipulated for the patient.

5. The method according to claim 1, wherein the mobile devices use the same application software which can be downloaded from the Internet for the purpose of initializing and/or controlling the ECG recorder and/or displaying the ECG profile, and their different authorizations are implemented by the ECG recorder using the certificate which is provided for the respective mobile device by the administration network.

6. The method according to claim 1, wherein the administration network provides two different certificates for each ECG recording, one certificate being a patient certificate assigned to the patient mobile device.

7. The method according to claim 1, wherein the administration network provides a certificate for each ECG recording, which certificate is used by all mobile devices for authorization for accessing the ECG recorder, in which case possibly different authorizations of the mobile devices are implemented at the level of the application software for initializing and/or controlling the ECG recorder and/or for displaying the ECG profile.

8. The method according to claim 1, wherein a patient application is installed on patient mobile device and a service application is installed on the other mobile devices, patient app providing reduced authorization for controlling and for receiving data from ECG recorder in comparison with the service application.

9. The method according to claim 1, wherein the patient mobile device is also used for GPS positioning of the patient.

10. The method according to claim 1, wherein in order to initialize the outpatient electrocardiography, the patient data required for this purpose are transmitted from a patient database inside the administration network to the first mobile device and are transmitted from there to the ECG recorder.

11. The method according to claim 1, wherein, when initializing the outpatient electrocardiography, the safe application of the ECG electrodes is checked and an error message including instructions for error correction is possibly transmitted to the first mobile device.

12. The method according to claim 1, wherein ECG data are transmitted from the ECG recorder to an ECG analysis system inside the administration network via the mobile devices for evaluation, the evaluation results, possibly including therapeutic recommendations, in turn being transmitted from the ECG analysis system to the mobile devices.

13. The method according to claim 1, wherein a near-field communication method, in particular Bluetooth or Wireless Local Area Network (WLAN), is used to transmit data between the mob devices and the administration network and/or between the mobile devices and the ECG recorder.

14. The method according to claim 1, wherein data are transmitted between the mobile devices and the administration network and/or between the mobile dev and the ECG recorder in encrypted form, in particular using two-fish encryption or the Hypertext Transfer Protocol Secure (HTTPS) protocol.

15. The method according to claim 1, wherein the storing of the ECG data and the certificates in the ECG recorder and in the administration network is done in encrypted form.

16. The method according to claim 1, wherein the certificates provided by the administration network are generated for a respective ECG recording as temporary certificates with a stipulated validity period.

17. The method according to claim 1, wherein the certificates provided by the administration network for an ECG recording using an ECG recorder are deleted after data have been transmitted to the ECG analysis system.

* * * * *